US012279599B2

(12) United States Patent
Chrobak et al.

(10) Patent No.: US 12,279,599 B2
(45) Date of Patent: Apr. 22, 2025

(54) TURBIDITY DETERMINATION USING COMPUTER VISION

(71) Applicant: TidalX AI Inc, San Ramon, CA (US)

(72) Inventors: Laura Valentine Chrobak, Menlo Park, CA (US); Peter Kimball, Mountain View, CA (US); Barnaby John James, Campbell, CA (US); Julia Black Ling, Menlo Park, CA (US)

(73) Assignee: TidalX AI Inc., Mountain View, CA (US)

( * ) Notice: Subject to any disclaimer, the term of this patent is extended or adjusted under 35 U.S.C. 154(b) by 104 days.

(21) Appl. No.: 18/349,449

(22) Filed: Jul. 10, 2023

(65) Prior Publication Data

US 2024/0147968 A1    May 9, 2024

Related U.S. Application Data

(63) Continuation of application No. 17/379,893, filed on Jul. 19, 2021, now Pat. No. 11,737,434.

(51) Int. Cl.
| | | |
|---|---|---|
| *A01K 61/95* | (2017.01) | |
| *A23K 50/80* | (2016.01) | |
| *G01N 21/53* | (2006.01) | |
| *G01N 33/18* | (2006.01) | |
| *G06F 18/22* | (2023.01) | |

(Continued)

(52) U.S. Cl.
CPC .............. *A01K 61/95* (2017.01); *A23K 50/80* (2016.05); *G01N 21/532* (2013.01); *G01N 21/534* (2013.01); *G01N 33/18* (2013.01); *G06F 18/22* (2023.01); *G06N 20/00* (2019.01); *G06V 40/10* (2022.01)

(58) Field of Classification Search
CPC ........ A01K 61/95; A23K 50/80; G06N 20/00; G06V 40/10; G06F 18/22; G01N 21/532; G01N 21/534; G01N 33/18
See application file for complete search history.

(56) References Cited

U.S. PATENT DOCUMENTS

| 5,828,458 A | 10/1998 | Taylor et al. |
|---|---|---|
| 7,142,299 B2 | 11/2006 | Tokhtuev et al. |
| 7,355,194 B2 | 4/2008 | Tobimatsu |

(Continued)

FOREIGN PATENT DOCUMENTS

| CL | 2019000039 A1 | 3/2019 |
|---|---|---|
| CN | 103499539 | 1/2014 |

(Continued)

OTHER PUBLICATIONS

Extended Search Report in European Appln. No. 22151132.2, dated May 2, 2022, 10 pages.

(Continued)

*Primary Examiner* — Mark Roz
(74) *Attorney, Agent, or Firm* — Fish & Richardson P.C.

(57) ABSTRACT

Methods, systems, and apparatus, including computer programs encoded on a computer storage medium, that generate from a first pair and a second pair of images of livestock that are within an enclosure and that are taken at different times using a stereoscopic camera, at least two distance distributions of the aquatic livestock within the enclosure. The distance distributions can be used to determine a measure associated with an optical property of the water within the enclosure. A signal associated with the measure can be provided.

20 Claims, 3 Drawing Sheets

(51) Int. Cl.
G06N 20/00 (2019.01)
G06V 40/10 (2022.01)

(56) References Cited

U.S. PATENT DOCUMENTS

| | | |
|---|---|---|
| 10,856,520 B1 | 12/2020 | Kozachenok et al. |
| 2006/0055927 A1 | 3/2006 | Feng |
| 2007/0151522 A1 | 7/2007 | Brauman |
| 2013/0044325 A1 | 2/2013 | Koyanagi |
| 2015/0308948 A1 | 10/2015 | Robitaille et al. |
| 2017/0150701 A1 | 6/2017 | Gilmore et al. |
| 2019/0228218 A1 | 7/2019 | Barnaby et al. |
| 2019/0340440 A1 | 11/2019 | Atwater et al. |
| 2020/0107524 A1 | 4/2020 | Messana et al. |
| 2020/0155882 A1 | 5/2020 | Tohidi et al. |
| 2020/0288678 A1 | 9/2020 | Howe et al. |
| 2021/0041368 A1 | 2/2021 | Lu et al. |
| 2021/0085165 A1 | 3/2021 | Rauniyar et al. |
| 2021/0329892 A1 | 10/2021 | Kozachenok et al. |
| 2022/0237799 A1 | 7/2022 | Price et al. |
| 2022/0400657 A1 | 12/2022 | Humphreys |

FOREIGN PATENT DOCUMENTS

| | | |
|---|---|---|
| CN | 106018408 | 10/2016 |
| CN | 108040948 | 5/2018 |
| EP | 2244934 | 11/2010 |
| EP | 3484283 | 5/2019 |
| GB | 2568501 | 5/2019 |
| JP | 2002171853 | 6/2002 |
| NO | 300401 | 5/1997 |
| NO | 20160199 | 8/2017 |
| WO | WO 1990/007874 | 7/1990 |
| WO | WO 1997/019587 | 6/1997 |
| WO | WO 2009/008733 | 1/2009 |
| WO | WO 2009/097057 | 8/2009 |
| WO | WO 2012/081990 | 6/2012 |
| WO | WO 2014/179482 | 11/2014 |
| WO | WO 2015/161748 | 10/2015 |
| WO | WO 2017/137896 | 8/2017 |
| WO | WO 2017/175261 | 10/2017 |
| WO | WO 2018/011744 | 1/2018 |
| WO | WO 2018/011745 | 1/2018 |
| WO | WO 2019/002881 | 1/2019 |
| WO | WO 2019/121851 | 6/2019 |
| WO | WO 2019/188506 | 10/2019 |
| WO | WO 2019/232247 | 12/2019 |
| WO | WO 2020/046524 | 3/2020 |
| WO | WO 2020/132031 | 6/2020 |
| WO | WO 2021/006744 | 1/2021 |
| WO | WO 2021/030237 | 2/2021 |
| WO | WO 2022/010815 | 1/2022 |
| WO | WO 2020/072438 | 4/2022 |

OTHER PUBLICATIONS

Garcia et al., "Monitoring and control sensor system for fish feeding in marine fish farms," IET Commun., Aug. 2011, 5(12):1682-1690.
International Preliminary Report on Patentability in International Appln. No. PCT/US2020/059829, dated May 27, 2022, 11 pages.
International Preliminary Report on Patentability in International Appln. No. PCT/US2022/032756, dated Feb. 1, 2024, 10 pages.
International Search Report and Written Opinion in International Appln No. PCT/US2022/018651, dated Jun. 22, 2022, 14 pages.
International Search Report and Written Opinion in International Appln No. PCT/US2022/021683, dated Jun. 27, 2022, 14 pages.
International Search Report and Written Opinion in International Appln No. PCT/US2022/022250, dated Jul. 6, 2022, 15 pages.
International Search Report and Written Opinion in International Appln No. PCT/US2022/022492, dated Jun. 28, 2022, 13 pages.
International Search Report and Written Opinion in International Appln No. PCT/US2022/022589, dated Jul. 7, 2022, 12 pages.
International Search Report and Written Opinion in International Appln No. PCT/US2022/022837, dated Aug. 2, 2022, 14 pages.
International Search Report and Written Opinion in International Appln No. PCT/US2022/023831, dated Jul. 8, 2022, 13 pages.
International Search Report and Written Opinion in International Appln. No. PCT/US2020/059829, dated Feb. 25, 2021, 18 pages.
International Search Report and Written Opinion in International Appln. No. PCT/US2022/032756, dated Nov. 18, 2022, 18 pages.
Invitation to Pay Additional Fees in International Appln. No. PCT/US2022/032756, dated Sep. 28, 2022, 10 pages.
Koehrsen ("Beyond Accuracy: Precision and Recall", willkoehrsen. github.io 2018) (Year: 2018).
Liu et al., "A Review of Turbidity Detection Based on Computer Vision," IEEE Access, Oct. 2018, 6:60586-60604.
Maloy et al., "A spatio-temporal recurrent network for salmon feeding action recognition from underwater videos in aquaculture," Computers and Electronics in Agriculture, Nov. 12, 2019, 9 pages.
Markussen, "Parchar—Characterization of Suspended Particles Through Image Processing in Matlab," Journal of Open Research Software, Jul. 1, 2016, 4(1):e26.
Meidell et al., "FishNet: A Unified Embedding for Salmon Recognition," Thesis for Master's degree in Artificial Intelligence, Norwegian University of Science and Technology, Jun. 2019, 86 pages.
Moskvyak et al., "Robust Re-identification of Manta Rays from Natural Markings by Learning Pose Invariant Embeddings," CoRR, Feb. 2019, arXiv:1902.10847v1, 12 pages.
Naval et al., "FishDrop: Estimation of reef fish population density and biomass using stereo cameras," 2016 Techno-Ocean (Techno-Ocean), Oct. 2016, pp. 527-531.
Odey, "AquaMesh—Design and Implementation of Smart Wireless Mesh Sensor Networks for Aquaculture," American Journal of Networks and Communications, Jul. 2013, 8 pages.
Petrov et al., "Overview of the application of computer vision technology in fish farming." E3S Web of Conferences, 2020, 175:02015.
Qiu et al., "Improving Transfer Learning and Squeeze-and-Excitation Networks for Small-Scale Fine-Grained Fish Image Classification," IEEE Access, Dec. 2018, 6(31):78503-78512.
Roser er al., "Simultaneous underwater visibility assessment, enhancement and improved stereo," 2014 IEEE International Conference on Robotics and Automation (ICRA), May 2014, pp. 3840-3847.
Saberloon et al., "Application of Machine Vision Systems in Aquaculture with Emphasis on Fish: State-of-the-Art and Key Issues," Reviews in Aquaculture, Dec. 2017, 9:369-387.
Stein et al., "Consistent melanophore spot patterns allow long-term individual recognition of Atlantic salmon *Salmo salar*," Journal of Fish Biology, Nov. 2017, 91(6):1699-1712.
towardsdatascience.com [online], "Analyzing Applications of Deep Learning in Aquaculture," Jan. 2021, retrieved on Aug. 11, 2021, retrieved from URL<https://towardsdatascience.com/analyzing-applications-of-deep-learning-in-aquaculture-7a273399553/>, 12 pages.
Turbidity and Water, USGS (Year: 2018).
Turbidity, Wikipedia (Year: 2004).
Wang, "Robust tracking of fish schools using CNN for head identification," Multimedia Tools and Applications, Nov. 2017, 20 pages.

TURBIDITY DETERMINATION USING COMPUTER VISION

CROSS-REFERENCE TO RELATED APPLICATIONS

This application is a continuation application of and claims the benefit of priority to U.S. application Ser. No. 17/379,893, filed on Jul. 19, 2021, the contents of which are hereby incorporated by reference.

TECHNICAL FIELD

This specification relates to determining optical properties of an environment, and one particular implementation relates to determining turbidity in an aquaculture environment using signals produced by a computer vision perception system associated with a biomass estimation subsystem.

BACKGROUND

Optical property detection systems use devices to measure optical properties of media such as water and air. For example, a Secchi disk can be used by a human operator to determine the turbidity of water, and technologies such as infrared forward-scatter technology, transmissometers, and light detection and ranging (LIDAR) can be used to measure a visibility range through air.

Optical properties in agriculture and aquaculture environments influence both the behavior of livestock and the management of the environment. For example, some livestock feed better when they can visually perceive food, so the level of illumination and the clarity of the environment influence their feeding behavior, and consequently, systems that control feeding within the environment. In addition, illumination and imaging devices can be integral parts of livestock management, and optical properties can influence the operation of such devices. For example, imaging devices can be used to measure the health of members of a livestock population, for example, by detecting parasitic infestations, but such devices can require proper levels of illumination.

However, existing approaches to measuring optical properties have drawbacks. For example, Secchi disks require manual involvement, which is not possible in an environment that is largely automated. Automated detection technologies such as refracted light system can require the introduction and maintenance of additional devices.

SUMMARY

This specification describes a framework implemented as computer programs on one or more computers in one or more locations that uses perception data, produced by applying computer vision techniques and configured for consumption by one environmental management system, to determine alternate properties of the environment, including optical properties such as turbidity. Such additional determinations can be made without introducing additional devices into the environment, and can be used to improve the management of the environment.

As one example, this specification describes a framework that determines turbidity within an aquaculture or agriculture environment by using data produced for biomass estimation by a perception system, to determine a level of turbidity in the water of a pen. The turbidity determination can then be used to guide environmental management actions. More specifically, the computer vision data used for biomass estimation are intercepted and reused to determine distance distributions of the livestock, and the distance distributions are used to determine turbidity levels. Once turbidity is determined, the framework can initiate livestock management actions such as adjusting the lighting settings of illumination devices, altering feeding schedules, sending alerts, correcting measurement made by other devices, etc.

Particular embodiments of the subject matter described in this specification can be implemented so as to realize one or more of the following advantages. The techniques described below can be used to determine optical properties of an environment, such as turbidity, by reusing data produced for an environmental system, thereby eliminating the need to introduce additional equipment to the environment. The techniques described below can further be used to determine turbidity as a function of depth or direction, which can be used, for example, to influence the operation of other environmental systems. Additionally, the techniques below can be used to determine turbidity without the need for calibration.

One aspect features generating from a first pair and a second pair of images of livestock that are within an enclosure and that are taken at different times using a stereoscopic camera, at least two distance distributions of the aquatic livestock within the enclosure. The distance distributions can be used to determine a measure associated with an optical property of the water within the enclosure. A signal associated with the measure can be provided.

Another aspect features obtaining a first signal produced for use by a first management subsystem, where the first management subsystem is configured to control at least one management operation within an agriculture or aquaculture environment. The first signal can be used to produce a second signal. The second signal can be provided to at least one second management subsystem. The second management subsystem can be configured to control at least a second management operation within an agriculture or aquaculture environment. The first management subsystem can be distinct from the second management subsystem.

One or more of the following features can be included. The optical property can be turbidity. The signal can be associated with a change in the operation of a feeding subsystem. Determining the measure associated with a measure of a property of the water can include determining the identification of each of a plurality of individual livestock, and determining from the identification of each of a plurality of individual livestock, a measure associated with a property of the water. Providing the signal further can include obtaining criteria associated with the measure associated with a property of the water, determining whether the criteria are satisfied, and based on determining that the criteria are satisfied, providing the signal. Determining whether the criteria are satisfied can include evaluating at least one rule or evaluating at least one trained machine learning model.

The details of one or more implementations of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
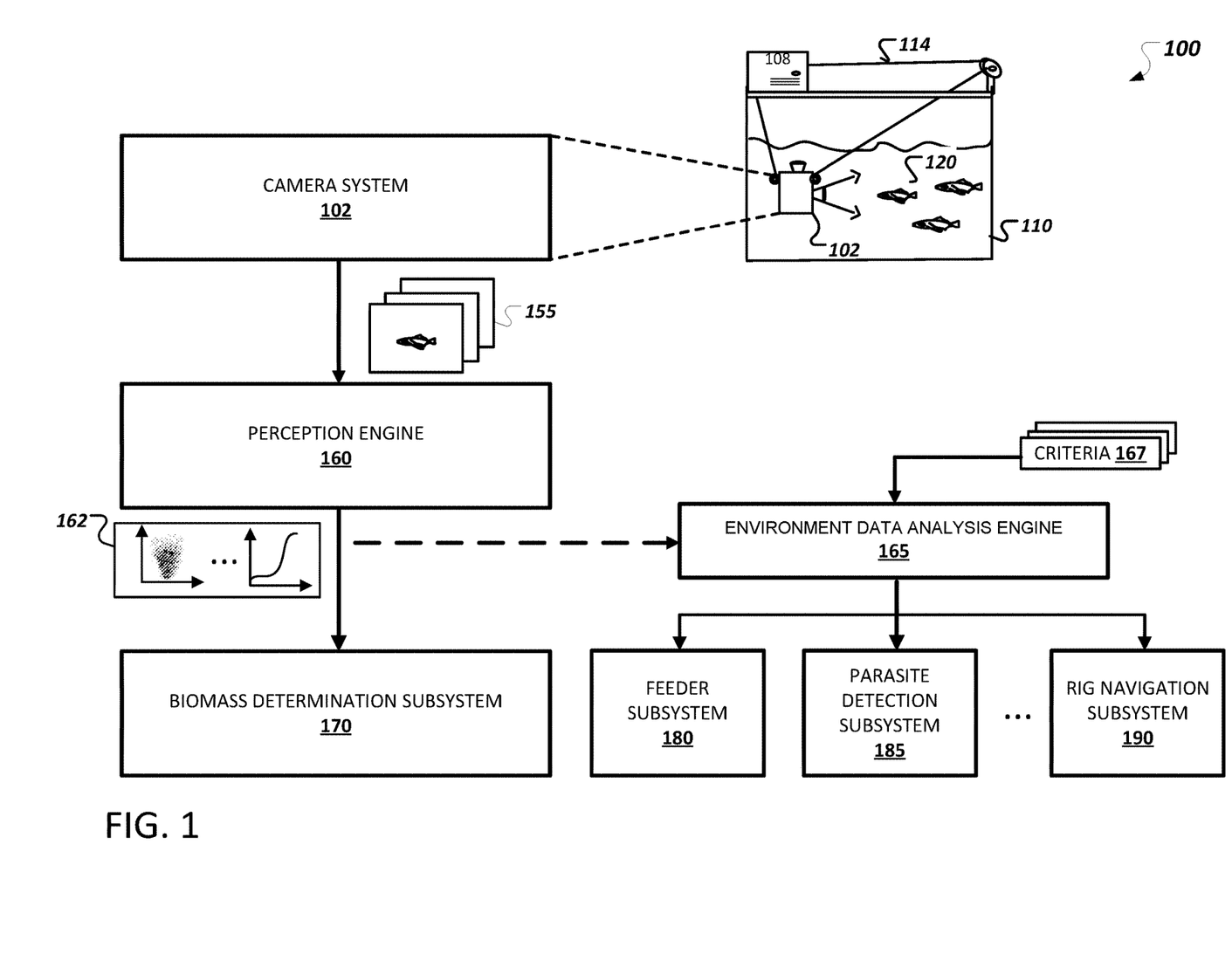
FIGS. 1 and 2 are diagrams of example systems for determining turbidity in an aquaculture environment using computer vision.

FIG. 1 is a diagram of an example system for determining turbidity in an aquaculture environment using computer vision. Aquaculture includes the farming of marine organisms such as fish, crustaceans and mollusks. Aquaculture is important to the health of marine ecosystems, which can suffer from overharvesting. Experience indicates over half of all fish and shellfish come from aquaculture, and in the absence of aquaculture, substantial, and perhaps irreversible, strain on marine ecosystems could result.

Some aquaculture environments use various sensors to aid in the care and feeding of the livestock. Sensors can provide measurements that are used to monitor environmental conditions such as light and temperature. The measurements can also be used when producing information such as estimates of the population of livestock, determinations of parasite infestations, and so on. Sensors can be attached in fixed positions, or attached to one or more rigs that patrol the environment.

Optical properties, particularly turbidity, can vary within an aquaculture environment for a variety of reasons. For example, turbidity can increase when foul weather causes floor sediment to circulate or when livestock detritus accumulates.

Changes in turbidity are relevant to effective management of an aquaculture environment. For example, fish typically feed more efficiently when they can visually perceive the food pellets, and turbidity reduces their ability to see the pellets; in more turbid conditions, a rig containing sensors might be instructed to seek clearer water, allowing the sensors to work more effectively; increases in turbidity can reduce the effectiveness of illumination devices, potentially requiring increases in illumination strength to enable proper imaging; and increases in turbidity can correlate with foul weather, so upon detecting turbidity, an alert can be raised to assist farmers.

However, introducing additional sensors to the environment can increase the complexity of managing the environment. Sensors can fail or become fouled in harsh aquatic environments, increasing the frequency of needed repairs, which can require a technician both to locate the faulty component and to replace or repair it. Further, additional equipment can produce electrical signals that increase electrical noise in the environment, which can affect the operation of delicate electronics in the environment.

With that introduction, FIG. 1 shows a system for determining turbidity in an aquaculture environment using perception data configured for and used by a biomass determination system. More specifically, the system determines livestock distance distributions from image data, produced by a perception system associated with a biomass estimation subsystem, to determine turbidity within an aquaculture environment.

The system 100 can include an enclosure 110 with a winch system 114 and one or more camera subsystems 102 each containing one or more cameras, including stereo cameras. The system 100 can also include one or more perception engines 160 and one or more environment data analysis engines 165. The perception engine 160 can provide environment data 162 to a biomass estimation subsystem 170 and to an environment data analysis engine 165, which in turn can provide signals to one or more environment management subsystems.

The enclosure 110 may enclose livestock that can be aquatic creatures, such as livestock 120, which swim freely within the confines of the enclosure 110. In some implementations, the aquatic livestock 120 stored within the enclosure 110 can include finfish or other aquatic lifeforms. The livestock 120 can include for example, juvenile fish, koi fish, sharks, salmon, bass, or crustaceans, e.g., shrimp, to name a few examples.

In addition to the aquatic livestock, the enclosure 110 contains water, e.g., seawater, freshwater, or rainwater, although the enclosure can contain any fluid that is capable of sustaining a habitable environment for the aquatic livestock.

In some implementations, the system 100 may be anchored to a structure such as a pier, dock, or buoy. For example, instead of being confined within the enclosure 110, the livestock 120 can be free to roam a body of water, and the system 100 can monitor livestock within a certain area of the body of water without the enclosure 110.

The winch subsystem 108 may move the camera subsystem 102 in a patrol pattern, e.g., up and down to different depths in the enclosure 110. For example, the camera subsystem 102 may patrol up and down within the enclosure 110 while it monitors fish feeding. The winch subsystem 108 can include one or more motors, one or more power supplies, and one or more pulleys to which the cord 114, which suspends the camera subsystem 102, is attached. A pulley is a machine used to support movement and direction of a cord, such as cord 114. Although the winch subsystem 108 includes a single cord 114, any configuration of one or more cords and one or more pulleys that allows the camera subsystem 102 to move and rotate, as described herein, can be used.

The winch subsystem 108 may activate one or more motors to move the cord 114. The cord 114, and the attached camera subsystem 102, can be moved along the x, y, and z-directions, to a position corresponding to the instruction. A motor of the winch subsystem 108 can be used to rotate the camera subsystem 102 to adjust the horizontal angle and the vertical angle of the sensor subsystem. A power supply can power the individual components of the winch subsystem. The power supply can provide AC and DC power to each of the components at varying voltage and current levels. In some implementations, the winch subsystem can include multiple winches or multiple motors to allow motion in the x, y, and z-directions.

Each camera subsystem 102 can include one or more image capture devices that can point in various directions, such as up, down, to any side, or at other angles. Each camera subsystem 102 can take images using any of its included imaging devices, and an enclosure 110 can contain multiple camera subsystems 102.

A camera subsystem 102 can provide image data 155, which can be individual image data or video image data, represented in any appropriate format. For individual images, formats can include JPEG, TIFF, BMP, raw, etc. For video image data, formats can include MP4, MOV, WAV, AVI, etc. The image data 155 can be provided to a perception engine 160.

The perception engine 160 can receive the image data 155 and apply computer vision models such as image classification, object detection, object tracking, etc., to produce environment data 162. The environmental data are produced for use by the biomass estimation system 170 and can be encoded in any suitable format such as Extensible Markup Language (XML), tabular form or binary encoding. The perception engine 160 can provide the environment data 162 to a biomass estimation system 170 and to an environment data analysis engine 165.

Environment data 162 can include any metric related to the environment or related to livestock within the environment. Examples of metrics can include counts of livestock, the tracks followed by livestock, identification of individual organisms, the average (mean, median and mode) distance of livestock from the camera, the distance distribution of livestock in relation to the camera, image quality, light level, the return strength of lighting in various frequency ranges, etc.

The biomass estimation system 170 can determine an approximation of the biomass within the environment from the environmental data 162. For example it is known that the weight of fish can be estimated based on fish tracks identified in images determined, for example, by sampling a random subset of the weights estimated from images, and continuing to randomly add more of the weights to the subset until the representative weight of the subset stabilizes. In addition, more efficient approach to determining a representative weight of the fish may be to prioritize sampling higher quality estimated weights. Biomass estimation is important both since the measurement of a biomass can influence feeding approaches, and since changes in biomass can reflect the health of livestock.

The environment data analysis engine 165 can use the environment data 162, produced for use by the biomass estimation system 170, to make additional inferences. In some implementations, criteria 167 can be applied to the inferences, and upon satisfaction of one or more criteria 167, signals can be provided to environmental subsystems such as feeder subsystems 180, parasite detection subsystems 185, rig navigation subsystems 190, etc. Inferences and criteria are described further in reference to FIG. 3. In other implementations, one or more machine learning models can be used to create the inferences, and the inferences can similarly be provided to environmental subsystems.

The environmental subsystem 180, 185, 190 can perform actions in response to receiving signals from the environment data analysis engine 165. For example, if turbidity is too high to capture accurate images, a parasite detection subsystem 185 can pause operation to conserve computing resource and to avoid producing spurious indications.

Figure 2:
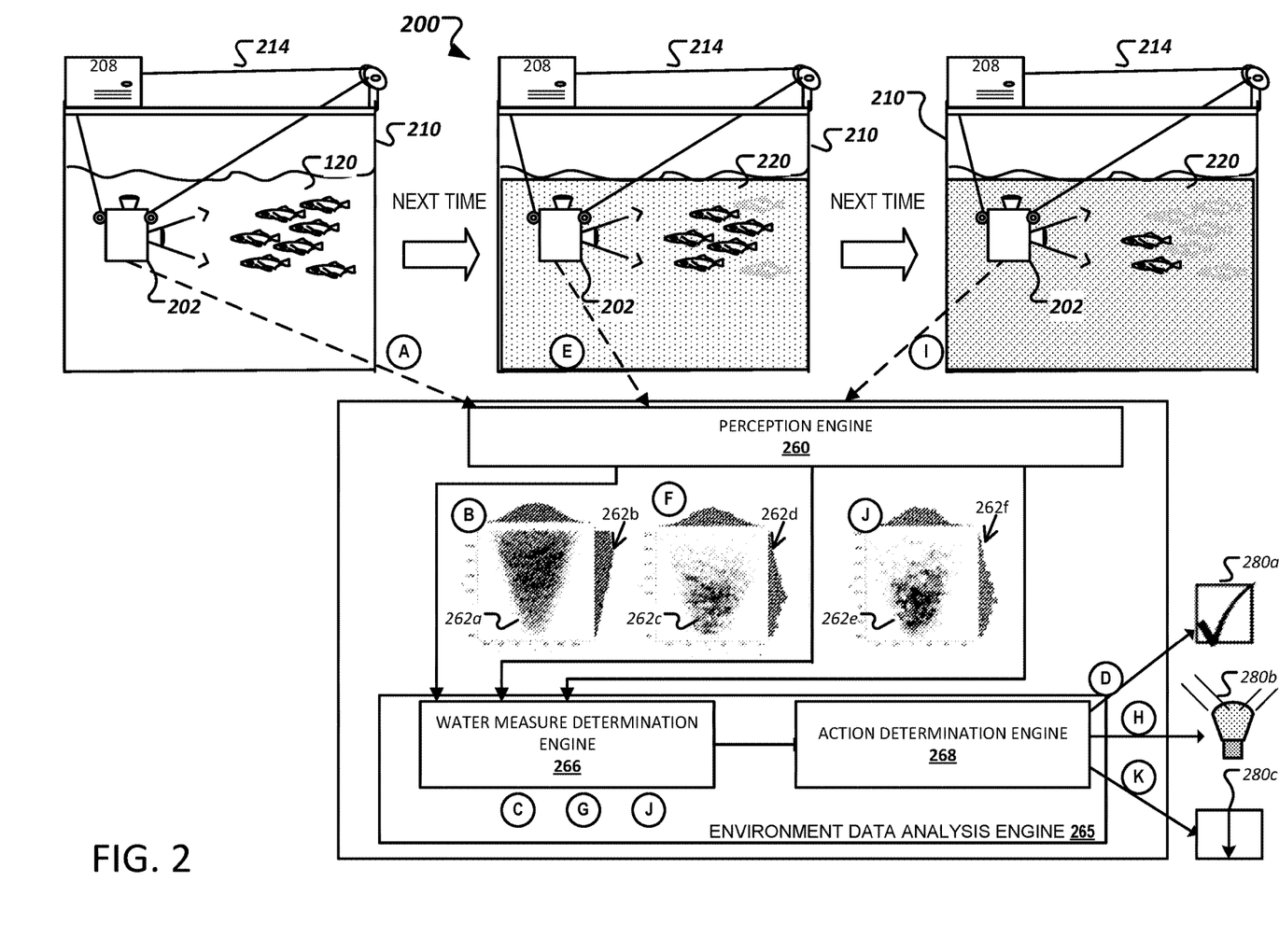

FIG. 2 is a diagram of an example system 200 for determining turbidity in an aquaculture environment using computer vision, and illustrates the system operating at three time periods.

The system 200 can include an enclosure 210, which can be, in some examples, the same type of enclosure as enclosure 110, with a winch system 214 and one or more camera subsystems 202. The system 200 can also include one or more perception engines 260 and an environment data analysis engine 265. The environment data analysis engine 265 can include a water measure determination engine 266 and an action determination engine 268. The environment data analysis engine 265 can produce signals 280a, 280b, 280c that are received by environment management subsystems such as the feeder subsystem 280, the parasite detection subsystem 285 and a rig navigation subsystem 290.

At a first time period, in step A, the camera subsystem 202 provides images to the perception engine 260. In step B, the perception engine 260 applies computer vision techniques such as object identification and object tracking to determine a distance distribution of the livestock in the vicinity of the camera subsystem 202.

The distance distribution can be represented in various formats including a scatterplot 262a and a plot 262b of a count of fish by the distance from the camera subsystem 202. Since the water is clear in this example, the camera subsystem has a clear view throughout its field of view, and the scatterplot 262a reflects a consistent distribution throughout the field of view of the camera subsystem 202, as illustrated by darker regions spread throughout the plot. (The scatterplot 262a shows relatively fewer fish in the immediate vicinity of the camera subsystem 202, reflecting an instinct of the fish to avoid unfamiliar objects.)

The plot 262b shows bars associated with fish counts at various distances from the camera, with the length of each bar correlated to the number of fish at the corresponding distance. The plot 262b reflects that the fish are spaced roughly evenly throughout the viewing area of the camera subsystem 202 (outside the immediate vicinity of the camera subsystem 202) as indicated by the similar lengths of the horizontal bars.

In step C, the water measure determination engine 266 can use the data reflected in scatterplot 262a and the plot 262b to determine that, outside the immediate vicinity of the camera subsystem 202, the distribution of fish is uniform. Since this uniformity is consistent with low turbidity, the water measure determination engine 266 can transmit to the action determination engine 268 a signal reflecting low turbidity. In step D, the action determination engine 268 can evaluate the signal against one or more criteria to determine one or more action signals. In this example, since turbidity is low, the action determination engine 268 can produce a signal 280a indicating, for example, that a feeder subsystem can operate nominally.

At a second time period, in step E, the camera subsystem 202 again provides images to the perception engine 260. In step F, the perception engine 260 applies computer vision techniques to determine a distance distribution.

In this time period, the camera subsystem has a slightly obscured view, so the scatterplot 262c reflects a less consistent distribution of fish throughout the field of view of the camera subsystem 202, and more specifically, fewer fish detected farther from the camera subsystem 202 as compared to the first scatterplot 262a, as illustrated by mix of lighter and darker regions in the plot. Such a plot is consistent with the camera subsystem 202 being unable to detect fish that are at a greater distance due to decreased visibility. The plot 262d reflects similar data with the distribution skewed more heavily to areas closer to the camera subsystem 202.

In step G, the water measure determination engine 266 can use the data reflected in the scatterplot 262c and the plot 262d to determine that, outside the immediate vicinity of the camera subsystem 202, the distribution of fish is non-uniform and skewed toward closer distances, which is consistent with increased turbidity. In response, the water measure determination engine 266 can transmit to the action determination engine 268 a signal reflecting increased turbidity. In step H, the action determination engine 268 can evaluate the signal against one or more criteria to determine action signals. In this example, since turbidity is increased, the action determination engine 268 can produce a signal 280b indicating, for example, that a parasite detection subsystem should increase the level of illumination to overcome the increased turbidity.

At a third time period, in step J, the camera subsystem 202 again provides images to the perception engine 260, and in step K, the perception engine 260 applies computer vision techniques to determine a distance distribution.

In this time period, the camera subsystem has a substantially obscured view, so the scatterplot 262e reflects a still more inconsistent distribution throughout the field of view of the camera subsystem 202, and more specifically, even fewer fish detected farther from the camera subsystem 202 as compared to the first and second scatterplots 262a, 262c. The plot 262d similarly reflects the situation with the distribution skewed even more heavily toward areas closer to the camera subsystem 202.

In step J, the water measure determination engine 266 can use the data reflected in scatterplot 262e and the plot 262f to determine that, outside the immediate vicinity of the camera subsystem 202, the distribution of fish is lower and less uniform, which is consistent with high turbidity. In response, the water measure determination engine 266 can transmit to the action determination engine 268 a signal reflecting increased turbidity. In step K, the action determination engine 268 can evaluate the signal against one or more criteria to determine action signals. In this example, since turbidity is high, the action determination engine 268 can produce a signal 280c indicating, for example, that a rig navigation subsystem should patrol in deeper water in search of less turbid conditions.

Figure 3:
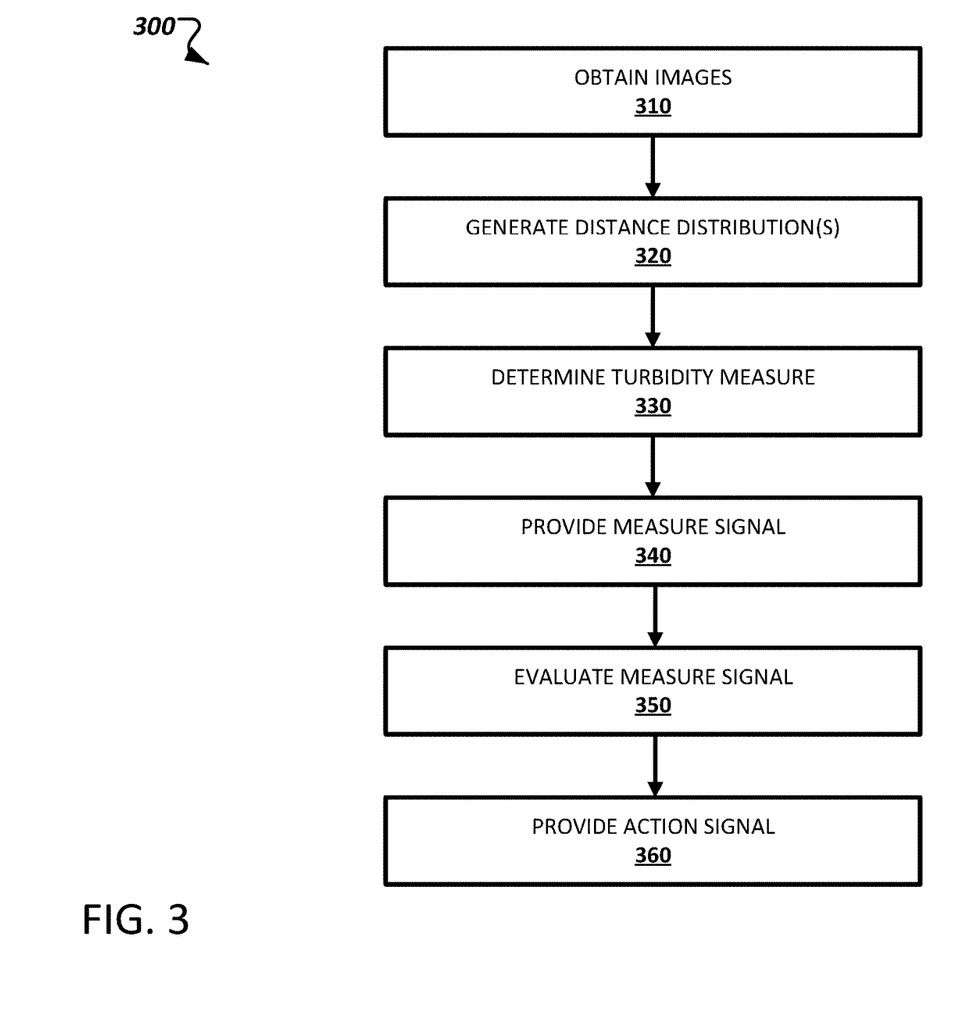
FIG. 3 is a flow diagram of an example process for determining turbidity of an aquaculture environment and providing the determination for use in managing the aquaculture environment.

FIG. 3 is a flow diagram of an example process for determining turbidity of an aquaculture environment and providing the determination for use in managing the aquaculture environment. For convenience, the process 300 will be described as being performed by a system for determining turbidity of an aquaculture environment, e.g., the system for determining turbidity of an aquaculture environment of FIG. 2, appropriately programmed to perform the process.

In operation 310, the system obtains images. Images can be obtained from a stereo camera subsystem, such as the camera subsystem 102 of FIGS. 1 and 2. Since the camera subsystem can contain a stereo camera, pairs of images can be obtained.

In operation 320, the system generates distance distributions for images. First, conventional object recognition techniques can be used to identify the position of each individual fish in the image. Then, the relative distance of each fish from the camera subsystem can be generated by determining the position on the Y-axis of the identified fish in the image. The absolute distance of the fish from the camera subsystem can be generated by multiplying the relative distance by a configured constant that reflects the reduction in scale between the image and the actual distance. Since the system can obtain pairs of images, one taken by each of two cameras in a stereo camera image, the distance can be computed using either image.

Optionally, the offset can be computed by determining the position on the X-axis of the identified fish in the image. The absolute distance of the fish from the camera subsystem can be generated by multiplying the relative offset by a configured constant that reflects the reduction in scale between the image and the actual distance. The offset can be measured from either camera in the stereo camera subsystem, provided the images from the same camera are used for all measurements.

Also optionally, the offset can be computed using the positions on both the X-axis and the Y-axis by applying the Pythagorean Theorem.

The distribution can be computed by aggregating the absolute distance data. To obtain a histogram, such as histograms 262b, 262d, 262f of FIG. 2, the distance data can be quantized. Similarly, data can be quantized to create scatterplots, such as scatterplots 262a, 262c, 262e of FIG. 2. Similarly, quantized data can be stored in memory, for example, in a data structure such as an array or vector of 1 dimension (for the histogram) or 2 dimensions (for the scatterplot). Data can be quantized into discrete distance measurements, such as into increments of 1 foot, 0.5 meter, 1.0 meter, etc.

In operation 330, the system determines a measure of turbidity in the environment. A measure of turbidity can be determined by computing the median distance of the fish from the camera subsystem. The median distance can be computed either from raw or quantized data. The median distance can also be computed across all measured distances, or it can be computed over measurements separated by depth or by direction, allowing the system to determine dependencies of the optical properties on depth or direction.

Optionally, changes in turbidity can also be determined by comparing the median computed distance between images taken at two or more time instances. Increases in the median distance can be associated with increased turbidity, and decreases in the median distance can be associated with decreased turbidity.

Also optionally, the rate of change of turbidity can be computed by dividing the change in turbidity by the elapsed time between the times the images were taken. Also optionally, acceleration (or deceleration) can be computed by dividing the rate of change of turbidity by the elapsed time between the times the images were taken. The rate of change and acceleration in change can be used in operation 350, described below.

In operation 340, the system provides a signal associated with the measure of turbidity. The signal can contain one or more metrics, such as a metric associated with turbidity, a quantized metric of turbidity (such as "high", "medium" and "low), a metric associated with the change in turbidity, a metric associated with the rate of change of turbidity, etc.

In optional operation 350, the system can evaluate the signal associated with the signal. The system can use various approaches to evaluating the signal. In some implementations, the system can use one or more trained machined learning models that process one or more signals as input and produce one or more scores associated with recommended actions.

In some implementations, the system can evaluate criteria that determine actions from signals. Criteria can be expressed as rules that, when satisfied, indicate a recommended action.

Recommended actions can relate to various aspects of aquaculture management. For example, when turbidity is determined to be extremely high, indicating that the camera might be rendered inoperable, the recommended action might indicate that the images produced should not be processed, reducing the computational load. In addition, the recommended action might indicate that the rig should patrol at different depths in search of clearer water. In another example, in moderate turbidity, the recommended action might indicate that illuminations devices should produce stronger lighting to compensate for the reduced clarity. Such an action can enable parasite detection to operate effectively despite suboptimal environmental conditions. Similarly, in response to detecting increased turbidity, since fish can eat less aggressively when they cannot see the feed, the recommended action can indicate that the feeding subsystem should reduce the quantity of feed released or the rate at which it is released. In still another example, if the turbidity is high, an indicator can be associated with the data produced by various subsystems, including the biomass estimation subsystem and the parasite detection subsystem reflecting lower confidence in the data. In yet another example, in high turbidity, the perception system itself might operate sub-optimally, incorrectly determining that multiple perceptions of the same fish are different fish.

Recommended actions can also be produced in response to changes and to rates of change in turbidity. For example, in response to sustained turbidity—that is, multiple images in which the average distance of the fish is below a configured threshold—a recommended action can indicate that the biomass estimation subsystem should increase the number of measurement days to compensate for lower visibility. In another example, if turbidity is high, but turbidity is trending lower, the recommended action can indicate that the feeder subsystem should delay feeding for some period.

In optional operation 360, the system can provide one or more recommended action signals associated with the evaluation of the turbidity signal to one or more aquaculture management subsystems, such as a feeder subsystem and a rig navigation subsystem. The signal can be provided over a network, such as the internet or a private network, using conventional communication protocols over a wired or wireless connection.

While this specification has largely focused on turbidity determined using data produced by a perception system associated with a biomass estimation subsystem, additional implementations are possible. For example, in some implementations, multiple abrupt changes to the distance distribution can indicate faults within one or more components of an environmental management system and can trigger an alert to a maintenance subsystem. Such an alert can also be used to add a marker to the images produced, indicating potential inaccuracies in the captured data.

Similarly, while this specification has described determined distance distributions to determine turbidity, other metrics can be used instead or in addition. For example, the average track lengths determined by a perception system can be reduced in increasingly turbid water. Therefore, the perception system can adjust its reported measurements, or associate a lower confidence value.

In addition, while this specification has largely described determining turbidity in an aquaculture environment, optical properties of an agriculture environment can also be determined. For example, a camera subsystem can be placed in an agriculture environment, and the species detected can be land animals such as cows, pigs, goats, etc. Changes to the determined distributions, and specifically a reduction in the number of animals detected at farther distances, can reflect environmental conditions such as rain, fog or smoke. An agriculture management system can react to such determinations, for example, by reducing feeding during rain, not processing images taken in heavy fog, and preparing a safe location for animals in the presence of smoke.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method comprising:
   receiving a first pair of images of an aquaculture environment, the first pair of images captured by a camera system at a first time;

receiving a second pair of images of the aquaculture environment, the second pair of images captured by the camera system at a second time different from the first time;

generating, from each of the first pair of images and the second pair of images, first and second respective distance distributions of one or more objects in the aquaculture environment, wherein each of the first and second respective distance distributions represents counts of objects at respective distances from the camera system;

determining, based on a comparison of the first and second distance distributions, a measure associated with an optical property of water in the aquaculture environment; and generating, based on the measure, a signal configured to activate one or more systems associated with the aquaculture environment.

2. The method of claim 1, wherein the optical property of the water is turbidity.

3. The method of claim 1, wherein the signal is associated with a change in operation of a feeding subsystem.

4. The method of claim 1, wherein determining the measure associated with the optical property of the water further comprises:

determining, using computer vision, an identification of each of the one or more objects in the environment; and determining, based on the identification of each of the one or more objects in aquaculture environment, the measure associated with the optical property of the water.

5. The method of claim 1, further comprising:

obtaining criteria associated with the measure associated with the optical property of the water;

determining whether the criteria are satisfied; and in response to determining that the criteria is satisfied, providing the signal.

6. The method of claim 5, wherein determining whether the criteria are satisfied includes evaluating the signal using at least one of (i) at least one rule, or (ii) at least one trained machine learning model.

7. A system comprising one or more computers and one or more storage devices storing instructions that when executed by the one or more computers cause the one or more computers to perform operations comprising:

receiving a first pair of images of an aquaculture environment, the first pair of images captured by a camera system at a first time;

receiving a second pair of images of the aquaculture environment, the second pair of images captured by the camera system at a second time different from the first time;

generating, from each of the first pair of images and the second pair of images, first and second respective distance distributions of one or more objects in the aquaculture environment, wherein each of the first and second respective distance distributions represents counts of objects at respective distances from the camera system;

determining, based on a comparison of the first and second distance distributions, a measure associated with an optical property of water in the aquaculture environment; and generating, based on the measure, a signal configured to active one or more systems associated with the aquaculture environment.

8. The system of claim 7, wherein the optical property of the water is turbidity.

9. The system of claim 7, wherein the signal is associated with a change in operation of a feeding subsystem.

10. The system of claim 7, wherein determining the measure associated with the optical property of the water further comprises:

determining, using computer vision, an identification of each of the one or more objects in the aquaculture environment; and determining, based on the identification of each of the one or more object in the aquaculture environment, the measure associated with the optical property of the water.

11. The system of claim 7, wherein providing the signal further comprises:

obtaining criteria associated with the measure associated with the optical property of the water;

determining whether the criteria are satisfied; and in response to determining that the criteria is satisfied, providing the signal.

12. One or more non-transitory computer-readable storage media storing instructions that when executed by one or more computers cause the one or more computers to perform operations comprising:

receiving a first pair of images of an aquaculture environment, the first pair of images captured by a camera system at a first time;

receiving a second pair of images of the aquaculture environment, the second pair of images captured by the camera system at a second time different from the first time;

generating, from each of the first pair of images and the second pair of images, first and second respective distance distributions of one or more objects in the aquaculture environment, wherein each of the first and second respective distance distributions represents counts of objects at respective distances from the camera system;

determining, based on a comparison of the first and second distance distributions, a measure associated with an optical property of water in the aquaculture environment; and generating, based on the measure, a signal configured to activate one or more systems associated with the aquaculture environment.

13. The one or more non-transitory computer-readable storage media of claim 12, wherein the optical property of the water is turbidity.

14. The one or more non-transitory computer-readable storage media of claim 12, wherein the signal is associated with a change in operation of a feeding subsystem.

15. The one or more non-transitory computer-readable storage media of claim 12, wherein determining the measure associated with a property of the water further comprises:

determining, using computer vision, an identification of each of the one or more objects in the environment; and determining, from the identification of each of the one or more objects in the environment, the measure associated with the optical property of the water.

16. The one or more non-transitory computer-readable storage media of claim 12, wherein the operations further comprise:

obtaining criteria associated with the measure associated with the optical property of the water;

determining whether the criteria are satisfied; and in response to determining that the criteria is satisfied, providing the signal.

17. The method of claim 1, wherein generating the first and second respective distance distributions of one or more objects in the aquaculture environment comprises, for each of the first and second respective distance distributions:

identifying, by a model configured to perform object recognition, the one or more objects in the environment;

determining, by one or more computing devices, a set of relative distances for the one or more objects from the respective pair of images, wherein each relative distance in the set of relative distances is an estimated distance between an object of the one or more objects and the camera system; and generating, by the one or more computing devices, a set of absolute distances for the one or more objects based on the set of relative distances and parameters of the camera system that captured the respective pair of images, wherein each absolute distance in the set of absolute distances represents an adjustment of the respective relative distance for an object in the one or more objects, wherein the adjustment of the respective relative distance is based on the parameters of the camera system.

18. The method of claim 17, wherein determining the measure associated with the optical property of the water comprises:

determining a first median distance for the first set of absolute distances for the first distance distribution and a second median distance for the second set of absolute distances for the second distance distribution;

comparing the first median distance to the second median distance;

based on the comparison of the first median distance to the second median distance, determining a rate of change for the optical property of the water; and determining the measure based on the rate of change for the optical property of the water.

19. The method of claim 1, wherein the signal is configured to adjust at least one lighting device associated with the aquaculture environment, trigger one or more alerts in a maintenance system associated with the aquaculture environment, affect an operation of a parasite detection system associated with the aquaculture environment, affect an operation of a navigation system associated with the camera device.

20. The method of claim 1, wherein the signal is configured to affect an operation of a biomass estimation system, and wherein affecting the operation of the biomass estimation system comprises:

assigning a confidence score of measurements captured by the biomass estimation system based on conditions of the aquaculture environment; and adjusting, based on the signal and the confidence score, a duration of time for capturing measurements by the biomass estimation system.

* * * * *

UNITED STATES PATENT AND TRADEMARK OFFICE
CERTIFICATE OF CORRECTION

| | | |
|---|---|---|
| PATENT NO. | : 12,279,599 B2 | Page 1 of 1 |
| APPLICATION NO. | : 18/349449 | |
| DATED | : April 22, 2025 | |
| INVENTOR(S) | : Laura Valentine Chrobak et al. | |

It is certified that error appears in the above-identified patent and that said Letters Patent is hereby corrected as shown below:

On the Title Page

Column 1 (Applicant):
Delete "Inc," and insert -- Inc., --

Signed and Sealed this
Tenth Day of June, 2025

Coke Morgan Stewart
*Acting Director of the United States Patent and Trademark Office*